(12) United States Patent
Burg et al.

(10) Patent No.: US 8,293,531 B1
(45) Date of Patent: Oct. 23, 2012

(54) THREE-DIMENSIONAL EX VIVO SYSTEM

(75) Inventors: Karen J. L. Burg, Clemson, SC (US); Chih-Chao Yang, Seneca, SC (US)

(73) Assignee: Clemson University Research Foundation, Clemson, SC (US)

( * ) Notice: Subject to any disclaimer, the term of this patent is extended or adjusted under 35 U.S.C. 154(b) by 918 days.

(21) Appl. No.: 12/201,297

(22) Filed: Aug. 29, 2008

Related U.S. Application Data

(60) Provisional application No. 60/967,054, filed on Aug. 31, 2007.

(51) Int. Cl.
*C12N 5/02* (2006.01)
(52) U.S. Cl. ........................................ 435/398
(58) Field of Classification Search ........................ None
See application file for complete search history.

(56) References Cited

U.S. PATENT DOCUMENTS

| | | | |
|---|---|---|---|
| 3,918,455 A | 11/1975 | Coplan | |
| 3,997,396 A | 12/1976 | Delente | |
| 4,027,676 A | 6/1977 | Mattei | |
| 5,123,912 A | 6/1992 | Kaplan et al. | |
| 5,162,225 A | 11/1992 | Sager et al. | |
| 5,200,248 A | 4/1993 | Thompson et al. | |
| 5,242,644 A | 9/1993 | Thompson et al. | |
| 5,263,984 A | 11/1993 | Li et al. | |
| 5,268,229 A | 12/1993 | Phillips et al. | |
| 5,512,600 A | 4/1996 | Mikos et al. | |
| 5,518,680 A | 5/1996 | Cima et al. | |
| 5,611,981 A | 3/1997 | Phillips et al. | |
| 5,716,404 A | 2/1998 | Vacanti et al. | |
| 5,723,159 A | 3/1998 | Phillips et al. | |
| 5,759,830 A | 6/1998 | Vacanti et al. | |
| 5,770,193 A | 6/1998 | Vacanti et al. | |
| 5,804,318 A | 9/1998 | Pinchuk et al. | |
| 5,906,828 A | 5/1999 | Cima et al. | |
| 5,942,436 A | 8/1999 | Dunn et al. | |
| 5,972,505 A | 10/1999 | Phillips et al. | |
| 6,206,930 B1 | 3/2001 | Burg et al. | |
| 6,303,136 B1 | 10/2001 | Li et al. | |
| 6,306,424 B1 | 10/2001 | Vyakarnam et al. | |
| 6,333,029 B1 | 12/2001 | Vyakarnam et al. | |
| 6,365,149 B2 * | 4/2002 | Vyakarnam et al. | 424/93.1 |
| 6,368,859 B1 | 4/2002 | Atala | |
| 6,468,649 B1 | 10/2002 | Zhong | |
| 6,521,431 B1 | 2/2003 | Kiser et al. | |
| 6,544,548 B1 | 4/2003 | Siller-Jackson et al. | |
| 6,666,893 B2 | 12/2003 | Burg et al. | |
| 6,753,311 B2 | 6/2004 | Fertala et al. | |
| 6,790,455 B2 | 9/2004 | Chu et al. | |
| 6,858,222 B2 | 2/2005 | Nelson | |
| 6,861,142 B1 | 3/2005 | Wilkie et al. | |
| 6,991,652 B2 * | 1/2006 | Burg | 623/8 |
| 7,056,580 B2 | 6/2006 | Dugan | |
| 7,118,909 B2 | 10/2006 | Gevaert et al. | |
| 7,374,673 B2 | 5/2008 | Marcus | |
| 2001/0033857 A1 | 10/2001 | Vyakarnam et al. | |
| 2002/0022883 A1 | 2/2002 | Burg | |
| 2002/0182720 A1 | 12/2002 | Gevaert et al. | |
| 2005/0070930 A1 | 3/2005 | Kammerer | |
| 2008/0293135 A1 | 11/2008 | Orr et al. | |

FOREIGN PATENT DOCUMENTS

JP     2-78629     3/1990

OTHER PUBLICATIONS

Sawhney, et al., "Bioerodible Hydrogels Based on Photopolymerized Poly(ethylene glycol)-co-poly(α-hydroxy acid) Diacrylate Macromers", *Macromolecules*, vol. 26, No. 4, (1993), pp. 581-587.
Conroy, et al., "Lubricious coatings for medical devices", *dds&s*, vol. 3, No. 4, pp. 89-92, (2004).
Harris, et al., "Assessment of the cytocompatibility of different coated titanium surfaces to fibroblasts and osteoblasts", *Cytocompatibility of Titanium Surfaces*, pp. 13-20 (2004).
Park, Joon Bu, *Biomaterials: An introduction*, pp. 230-231, 1992.
Ratner, et al, *Buiomaterials Science, An Introduction to Materials in Medicine*, pp. 170-173, 1996.

\* cited by examiner

*Primary Examiner* — Tekchand Saidha
*Assistant Examiner* — Younus Meah
(74) *Attorney, Agent, or Firm* — Dority & Manning, P.A.

(57) ABSTRACT

Disclosed are three-dimensional (3D) systems as may be utilized for ex vivo tissue or cell growth and development. A system generally includes a base material and at least one wicking fiber embedded therein through which a liquid can be spontaneously drawn by capillary action. Wicking fibers can define a plurality of colinear channels along the exterior surface of the axial length of the fiber. Wicking fibers can be present in disclosed systems as individual fibers or in bundles. Disclosed systems can be useful in various scientific studies, including, but not limited to, drug discovery, vaccine development, cell biology studies, and biomaterial development.

16 Claims, 3 Drawing Sheets

THREE-DIMENSIONAL EX VIVO SYSTEM

CROSS REFERENCE TO RELATED APPLICATION

The present application claims filing benefit of U.S. Provisional Patent Application Ser. No. 60/967,054 having a filing date of Aug. 31, 2007, which is incorporated herein in its entirety.

FEDERALLY SPONSORED RESEARCH AND DEVELOPMENT

The U.S. Government has a paid-up license in this invention and the right in limited circumstances to require the patent owner to license others on reasonable terms as provided for by the terms of Contract No. W81XWH-05-1-0379 awarded by the Department of Defense.

BACKGROUND

Model systems are known to be useful in connection with various biological studies or in clinical application such as liver dialysis. For instance, a model system may be developed to mimic skin tissue in order to study the migration of carcinogens through the skin. However, a problem exists with respect to many known biological model systems in that known models have been unable to facilitate transfer of fluid materials between and among cells once cell growth reaches a certain thickness or density. In effect, fluids are unable to penetrate a thicker concentration of cells or a denser scaffold/base. This deficiency is a particular area of concern because a high concentration of cells can more closely mimic an in vivo tissue environment.

Accordingly, a need exists for ex vivo and in vitro systems that can provide an environment for concentrated cell or tissue growth and simultaneously facilitate transportation of fluids between and among cells in the system.

SUMMARY

According to one embodiment, disclosed is a three-dimensional ex vivo system comprising a base material and at least one wicking fiber embedded therein, wherein the system supports the growth and development of ex vivo cells.

For example, a wicking fiber as may be utilized in a system can define a plurality of colinear channels on the exterior surface of the fiber. According to one embodiment, a wicking fiber can be hollow. Wicking fibers can be utilized alone or combined together in bundles.

A base material can be a hydrogel material, an alginate sponge, or the like.

A system can include additional materials as well, for instance biologically active materials that can affect a developing culture held within a system.

According to another embodiment, disclosed is a method for developing an ex vivo culture utilizing systems as disclosed herein. In particular, fluid transport within a system can include flow via capillary action along the axial length of a wicking fiber embedded within the base material of a system.

Disclosed methods can be used for growth and development of individual cells, a tissue explant, or a variety of different cell types.

BRIEF DESCRIPTION OF THE FIGURES

The present invention will become more fully understood from the detailed description and the accompanying drawings, wherein.

DETAILED DESCRIPTION

Reference will now be made in detail to various embodiments of the disclosed subject matter, one or more examples of which are set forth below. Each embodiment is provided by way of explanation of the subject matter, not limitation thereof. In fact, it will be apparent to those skilled in the art that various modifications and variations may be made in the present disclosure without departing from the scope or spirit of the subject matter. For instance, features illustrated or described as part of one embodiment, may be used in another embodiment to yield a still further embodiment.

In general, disclosed herein are three-dimensional (3D) systems as may be utilized in one embodiment for ex vivo tissue or cell growth. More specifically, a system as disclosed herein can include a base material and at least one wicking fiber embedded therein through which a liquid can be spontaneously drawn by capillary action, i.e., when the adhesive intermolecular forces between the liquid and the fiber surface are stronger than the cohesive intermolecular forces inside the liquid. Disclosed systems can be useful in various scientific studies, including, but not limited to, drug discovery, vaccine development, cell biology studies, and biomaterial development.

Among other beneficial characteristics, disclosed systems including one or more wicking fibers can provide for enhanced movement of materials through a cellular construct. For instance, disclosed systems can provide enhance movement of materials such as nutrients, cell signals, and waste products throughout the volume of a developing ex vivo or in vitro system.

Figure 1:
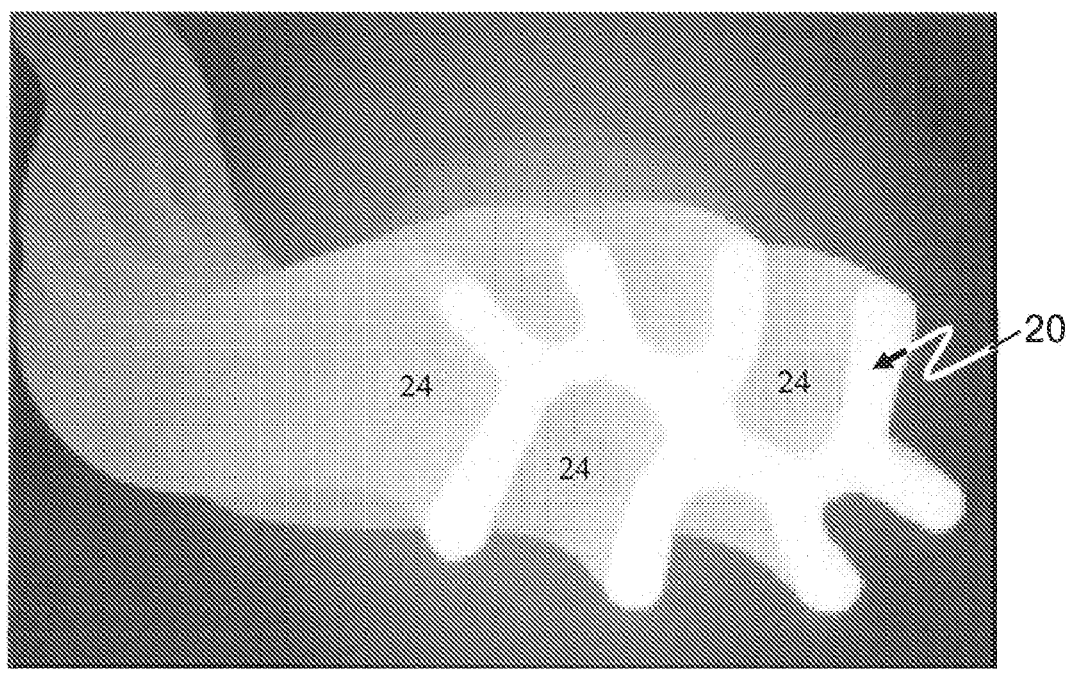
FIG. 1 is a schematic representation of one embodiment of a grooved fiber as may be utilized in disclosed systems.

As shown schematically in cross-section in FIG. 1, a fiber 20 can include multiple co-linear channels 24 extending the entire length of the exterior surface of the fiber 20. Each channel 24 is defined by walls that extend generally and longitudinally and form part of the exterior surface of the fiber 20. Desirably, the channels 24 extend down the entire length of the fiber 20 parallel to the longitudinal axis of the fiber 20 and are co-linear on each fiber 20.

In an alternative embodiment, the channels 24 can be configured to wrap around the length of the fiber 20 in a helical fashion. However, substantially all of the channels 24 will still be co-linear on each fiber 20

Figure 2:
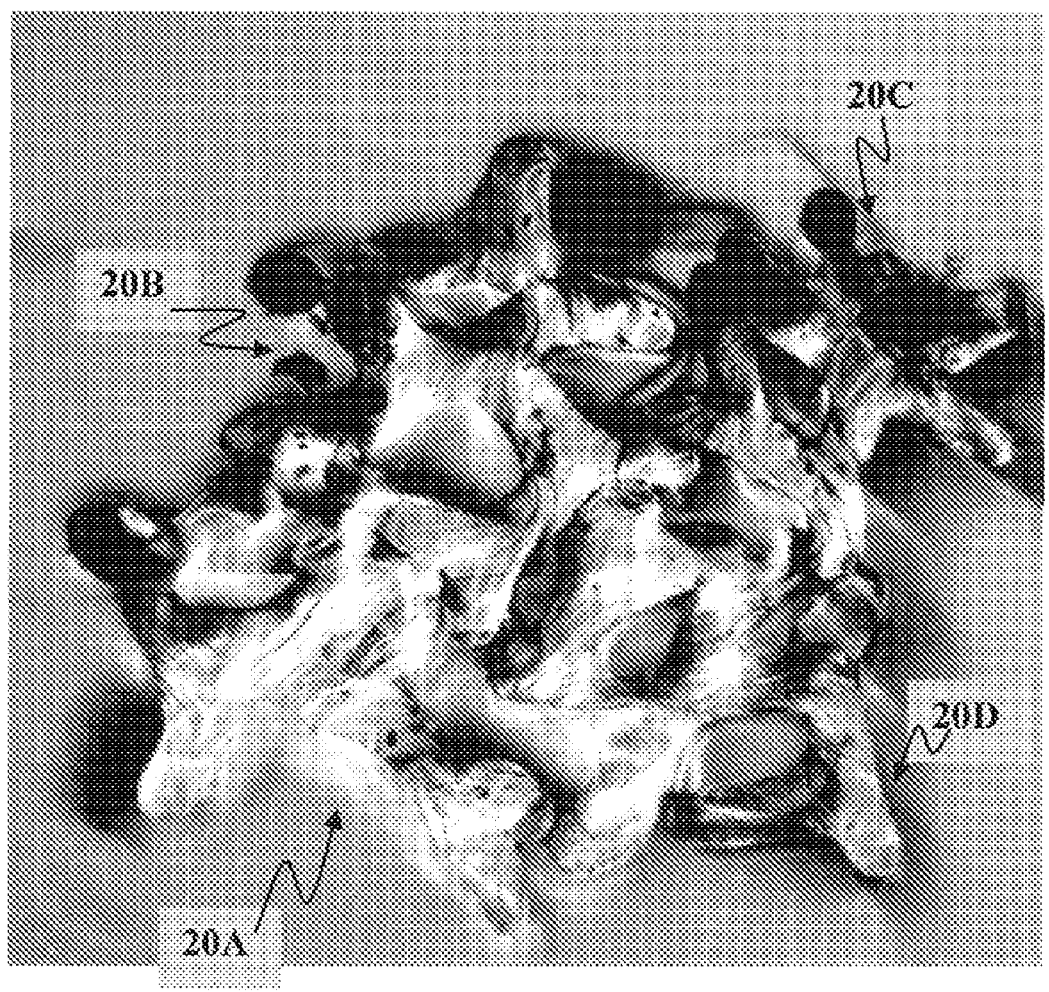
FIG. 2 is a photograph of a 4 fiber bundle in cross-section.

Wicking fibers can be embedded in a base material of a disclosed system as individual fibers or as bundles of wicking fibers, as desired. For instance, FIG. 2 illustrates a bundle of fibers including 4 channeled fibers 20A, 20B, 20C, and 20D. In the course of packing a plurality of fibers 20A, 20B, 20C, 20D into a bundle that can then be embedded within a base material, whether the individual fibers have purely linear channels 24 or helical channels, it is possible that one or more, even all, of the fibers in a bundle can rotate about its/their own axis over the entire length of the fiber bundle. In other words, the surface-channeled fibers 20 may twist as they lay within a base material. Accordingly, the channels 24 of the fibers also may twist somewhat.

Figure 3:
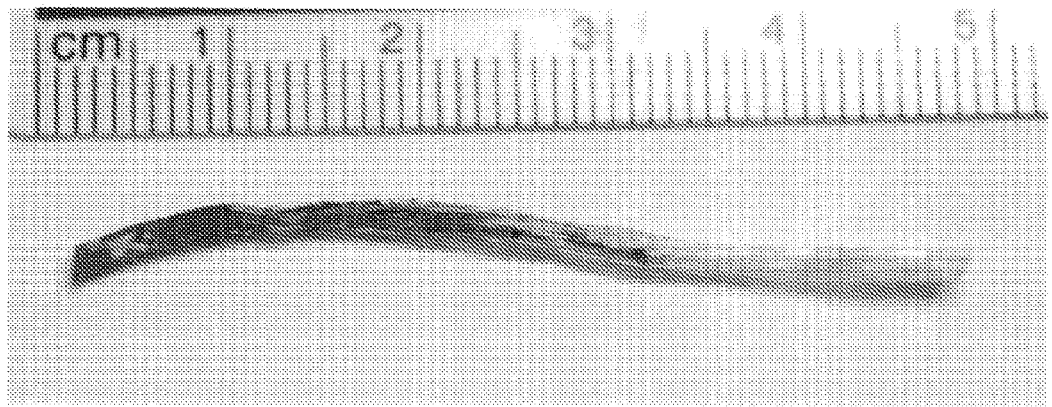
FIG. 3 is a photograph of a 4 fiber bundle following a capillary action test.
Figure 4:
FIG. 4 is a photograph of a 16 fiber bundle following a capillary action test.

Bundles of wicking fibers can effectively move fluid through the bundle via capillary action. For example, FIG. 3 illustrates a 4 fiber bundle following a capillary action test, and FIG. 4 illustrates a 16 fiber bundle following a capillary action test. Capillary actions tests carried out were similar to those described in the Example section, below.

Examples of wicking fibers suitable for use in the present invention include, but are not limited to, lobed, grooved or channeled fibers that can promote fluid movement via capillary action along the fiber when the fiber is embedded within a base material. Exemplary fibers can include, but are not limited to, fibers such as those disclosed in U.S. Pat. No. 5,200,248 to Thompson, et al. and U.S. Pat. No. 5,972,505 to Phillips, et al, the subject matter of each of which is incorporated herein by reference. However, disclosed subject matter is not limited to these specific embodiments. For instance, in another embodiment, wicking fibers as may be incorporated in disclosed systems can be hollow fibers that can wick fluid through one or more channels within the fiber, i.e., channels that are surrounded in cross section by fiber material.

There are different fabrication approaches to form wicking fibers of the sort demonstrated here. For example, a process used to make these disclosed wicking fibers can be amenable to any polymers that can be spin-melted. For example, channeled fibers 20 may be melt spun from any of a number of different biocompatible materials. A non-limiting listing of synthetic materials as may be utilized in forming disclosed wicking fibers can include chondroitin sulfate (a proteoglycan component), polyesters, polyethylene glycols, polycarbonates, polyvinyl alcohols, polyacrylamides, polyamides, polyacrylates, polyetheresters, polymethacrylates, polyurethanes, polycaprolactone, polyphophazenes, polyorthoesters, polystyrene, glass, copolymers of lysine and lactic acid, copolymers of lysine-RGD and lactic acid, and the like, and copolymers of the same.

Examples of naturally derived materials as may be utilized in forming a substrate include, but are not limited to, chitosan, agarose, alginate, gelatin collagen, hyaluronic acid, fibrin, dextran, carrageenan (a carboxylated seaweed polysaccharide), demineralized bone matrix, and the like, and copolymers of the same.

An array of fibers of differing chemistries, surface charges, dimensions, cross sections may be incorporated to provide fluid transport gradients. Fibers with gradient properties (along the length of the fiber) may also be employed.

According to the present disclosure, a system can include one or more wicking fibers embedded in a base material. Selection of the base material may vary depending on the particular end use application. In one embodiment, a base material can be a liquid or a viscous fluid that can form a gel matrix or a viscous fluid matrix. As utilized herein, the term "gel matrix" generally refers to a colloid in which a dispersed phase (e.g., a crosslinked polymer) is in combination with a continuous phase (e.g., water) to produce a viscous semisolid jellylike product. There are different methods of crosslinking or otherwise binding a dispersed phase of a gel as may be utilized as described herein. For example, a chemical crosslinking agent may be used or crosslinking may occur upon shift in pH or temperature.

Combinations of materials can also be utilized in disclosed base material. By way of example, a combination of alginate and gelatin can be used as a base material in one embodiment. As utilized herein, the term 'gelatin' generally refers to a thermo-reversible gel that can return to the liquid state upon temperature increase. This characteristic can be useful in creating porous structure within a base material.

A base material may include one or more materials which can be biodegradable or non-biodegradable, absorbable or non-absorbable, and so forth. A base material may be made from naturally derived materials, synthetic materials, or a combination thereof. A base material may also be cellular or acellular. For instance, cells or tissues or cellular extracts can be incorporated into a base material during the preparation of the base material according to standard methods.

Examples of suitable materials for a base material can include, but are not limited to, agarose, alginate, collagen, carrageenan (a carboxylated seaweed polysaccharide), chitosan and derivatives thereof. Examples of suitable biodegradable or absorbable biocompatible materials as may be included in a base material can include, but are not limited to, derivatives of polylactide, chondroitin sulfate (a proteoglycan component), polyesters, polyethylene glycols, polycarbonates, polyvinyl alcohols, polyacrylamides, polyamides, polyacrylates, polyesters, polyetheresters, polymethacrylates, polyurethanes, polycaprolactone, polyphophazenes, polyorthoesters, polyglycolide, copolymers of lysine and lactic acid, copolymers of lysine-RGD and lactic acid, dextran, dextrin, starch, cellulose, chitosan, demineralized bone matrix and the like and copolymers of the same.

According to one embodiment, a base material can be a non-biodegradable material formed by hydrating the triblock polymer poly(ethylene oxide)-polypropylene oxide)poly(ethylene oxide), which is commercially available under the PLURONIC™ or POLOXAMER™ trade names. Other base material materials can include those disclosed by Sawhney et al. (Macromolecules, 26:581 589 (1993)), which is incorporated herein by reference that include synthesized macromers having a poly(ethylene glycol) central block, extended with oligomers of α-hydroxy acids such as oligo(d,l-lactic acid) or oligo(glycolic acid) and terminated with acrylate groups. Such macromers can be rapidly polymerized with visible light in the presence of a non-toxic photoinitiator to form crosslinked gels. Gels can degrade within a physiological-like environment upon hydrolysis of the oligo(α-hydroxy acid) regions into poly(ethylene glycol), α-hydroxy acid, and oligo(acrylic acid). The degradation rates can be tailored by appropriate choice of the oligo(α-hydroxy acid). Another synthesized biodegradable block copolymeric material as can be utilized as a base material is disclosed in Japanese Patent No. 2-78629 (which is incorporated herein by reference), which is synthesized by transesterification of poly(lactic acid) (PLA) or poly(lactic acid)/glycolic acid (PLA/GA) and polyethylene glycol) (PEG). Base material materials are not limited to these specifically disclosed materials, however.

According to one embodiment, a base material can be a hydrogel. Hydrogels are water-swollen and cross-linked polymeric structures, usually having low modulus and compressive strength. Collagen is known to be an excellent hydrogel matrix material and has been found in diverse applications in regenerative medicine due to its biocompatibility and biodegradability. Collagen gels have been frequently used to provide attractive environments for normal cell growth. Mammary cells such as MAC-T cells (the MAC-T line is an immortalized epithelial cell line isolated from bovine mammary tissue) may be cultured in collagen gels in order to observe how the cells proliferate and differentiate in a 3D environment and to better understand breast cancer progression. Alginate, a polysaccharide extracted from seaweed, has been used widely in tissue engineering applications due to its ability to gently gel in the presence of divalent ions such as calcium chloride. Both collagen and alginate can encapsulate or transport cells. Thus, hydrogels have found widespread use in biomedical applications.

According to another embodiment, a base material can include an alginate sponge. Alginate sponges are highly porous, lyophilized substances with a lengthy history of use in connection with cell culture. The alginate base of a sponge generally refers to pharmaceutical-grade plant-derived alginate. Pore size and shape is generally homogenous, with pores ranging from 50 to 200 μm in size. Additionally, pores may be interconnecting.

In accordance with one embodiment of the present invention, wicking fibers can be incorporated into an alginate sponge, for instance to facilitate scale-up and development of cells. An alginate sponge structure can advantageously provide scaffolding for cell growth and development. One example of a conventional alginate sponge for use as described herein is the ALGIMATRIX™ 3D Culture System, which is available from Invitrogen Corporation of Carlsbad, Calif. Thus, in one aspect a base material can be an alginate sponge wherein wicking fibers can be inserted, for instance in parallel with one another or in one or more bundles. The fibers can improve the transfer of fluids between cells growing in the sponge-like base material.

A system including one or more wicking fibers and a base material can be loaded with one or more biologically active materials therein including cells, tissue explants, cellular extracts, and the like, which can be intended for growth and further proliferation within a system. Cellular extracts that may be incorporated into the substrates, the base material, or both can include, but are not limited to, deoxyribonucleic acid (DNA), plasmids, ribonucleic acid (RNA), growth factors, lipids, suspect carcinogens, and suspect mutagens. Biological materials as can be incorporated in a system can be homogeneous from one single source, or from different sources. According to an embodiment in which multiple different cell types are included in a system, a system can include substrates of different materials, each supporting a different type of cell or tissue. Alternatively, different cell types may be homogeneously distributed on substrates formed of the same materials.

Various techniques for isolating cells or tissues from suitable sources are generally known in the art, any of which can be utilized in conjunction with disclosed systems. Moreover, cells or tissues used as disclosed herein can be autologous, obtained from a living subject about which information is to be obtained from the system, or the cells can be allogenic, i.e., obtained from a subject of same species, but not the individual patient being examined. Materials can also be xenogenic, i.e., from a subject of different species than that for which information is being obtained or developed.

To promote the growth and differentiation of cells in a system, suitable signal molecules can be added to a culture medium, or to a constructed system, to promote cell adhesion, growth, and migration. Examples of such signal molecules include, but are not limited to, serum, growth factors, and extracellular matrix proteins.

Cells can be genetically, physically or chemically modified prior or subsequent to being incorporated into a disclosed system. Genetic modification by molecular biology techniques is generally known in the art, any of which are encompassed herein. Methods are also known in the art to modify the immunological characters of allogenic or xenogenic cells. Immunologically inert cells, such as stem cells, infant cells, and embryonic cells can be used in conjunction with other cell types according to one embodiment, for instance to avoid immunological incompatibility.

A wicking fiber and/or a base material may include biologically active compounds as may affect a system. For instance, a system can include a biologically active compound that can act as a signal for modifying cell adhesion, growth, or migration, preferably stimulating or promoting the adhesion, growth, or migration of the desirable cells, and/or inhibiting or stimulating the adhesion, growth, or migration of undesirable cells. Such compounds can include growth factors, hormones, extracellular matrix proteins and other cellular adhesion peptides identified in the extracellular matrix protein. Suitable growth factors may include, for example, epithelial growth factor (EGF), acidic or basic fibroblast growth factor (FGF), vascular endothelial growth factor (VEGF), hepatocyte growth factor (HGF), heparin binding growth factor (HGBF), transforming growth factor (TGF), nerve growth factor (NGF), muscle morphogenic factor (MMP), and platelet derived growth factor (PDGF). Examples of extracellular matrix proteins include fibronectin, collagens, laminins, and vitronectins, and the tri-peptide RGD (arginine-glycine-aspartate) that is found in many of the extracellular matrix proteins. A signal can also be included to induce the ingrowth of desirable cells, e.g., smooth muscle cells and epithelial cells. Compounds that inhibit or stimulate undesired cells, such as cancerous cells or inflammatory cells can be included.

Compounds can be covalently linked to a material to a fiber and/or base material, or associated with a fiber and/or base material by affinity, or linked to a material that itself can be covalently linked to or associated by affinity with a material in a fiber and/or base material. Alternatively, compounds can be dispersed in or in admixture with the base material or fibers following test system construction.

Systems and materials incorporated therein can be sterilized according to any suitable technique. Examples of such techniques include, but are not limited to, UV irradiation, gamma irradiation, e-beam sterilization and sterilization using chemicals such as ethylene oxide.

An ex vivo system as disclosed herein can be applicable across a wide range of specific end use applications that include, but are not limited to, breast, skin, hernia mesh, vascular graft, heart valve, ligament, tendon, and bone. An ex vivo system can provide a platform for drug discovery, vaccine development, and detailed study of cell-cell interactions and developmental cell biology studies.

According to one embodiment, an ex vivo tissue system can be in the form of a fiber reactor suitable, for example, for cell scale-up and/or for therapeutic extraction. In the case of cell scale-up, cells can be seeded on or in wicking fibers and allowed to multiply until a sufficient number has been reached, after which time the cells can be extracted for instance, for use in a secondary process. In the case of therapeutic extraction, cells can be seeded on or in wicking fibers and allowed to multiply. Products generated by the cells, such as protein therapeutics agents or growth factors, can be retrieved from the reactor over time and the cells can remain in the reactor long term.

There are numerous types of known fiber reactors, any of which can be improved through incorporation of a system as disclosed herein. For example, according to one preferred aspect of disclosed subject matter, wicking fibers can be utilized in place of non-wicking, round fibers as are found in a conventional hollow fiber bioreactor system. Wicking fibers can increase fiber surface area for scale-up as well as can allow wicking of liquids to cells held within a system. Cells can be seeded on the hollow fibers, which can appear as a cluster of parallel straw-like structures within a bioreactor. As cells are grown and developed, cells can release useful compounds that can then be removed from the bioreactor.

According to one embodiment, a system as disclosed herein can be incorporated into a dialysis process, as is known in the art. During dialysis, the blood is separated into plasma and cellular components. The separated plasma is passed through an absorbent activated charcoal filter to remove small molecular weight toxins. The detoxified plasma is then oxygenated and passes through a hollow fiber cartridge that houses living porcine liver cells. The live porcine liver cells are immobilized in the cartridge by a semi-porous membrane, and will eliminate further toxins, while also enriching the plasma with albumin and other proteins and providing additional liver-specific functions. The normalized, enriched plasma is then reunited with the blood cellular components and returned to the patient.

According to one preferred aspect of the present disclosure, wicking fibers can be incorporated in a fiber bioreactor, such as that described above with regard to a dialysis system. Incorporating of one or more wicking fibers in a fiber bioreactor can enhance drug delivery and fluid transfer between cells in the system, can enhance cell production and function, as well as any combination thereof.

According to another embodiment, wicking fibers may be added to a volume of cellular scaffolds in a modular bioreactor assembly in order to improve fluid transport through the volume. A modular bioreactor assembly may have a porous volume of, for example, poly-L-lactide hollow beads within a biochamber. By way of example, such an assembly may be useful in connection with stem cell growth on beads for purposes of developing bone tissue. In particular, the addition of wicking fibers to an assembly can enhance fluid transport through the system for fluids that include, but are not limited to, nutrients and waste.

In another preferred embodiment, an ex vivo system can be in the form of a wicking fiber or a fiber bundle loaded scaffold (cellular or acellular) used for purposes such as to better understand cellular behavior and mechanisms. The fiber or fiber bundle loaded scaffold can also be used to generate populations of cells in a consistent manner in order to study responses to or by those specific cells.

The presently disclosed subject matter may be better understood with reference to the following examples.

EXAMPLE 1

A fiber extruder was preheated to 140° C., and Tecoflex™ polymer was loaded into the extruder from the top. After 10 minutes of preheating, the temperature in the extruder was increased to 160° C. and held for 15 minutes.

Following the heating period, a weight was loaded from the top of the heating chamber, and extruded fibers were retrieved from the bottom of the extruder. Both wicking fibers and round cross-sectional fibers were formed. Fibers were cut to an appropriate length and held over night to regain elasticity prior to testing.

To carry out a capillary action test, 1 mL of 2% gelatin solution was placed in a well of a 24-well plate, and held in a refrigerator until the solution gelled. 4 fibers (either all wicking fibers or all round fibers) cut to a length of 2.5 cm were twisted until they adhered to one another. Each bundle of fibers was bent to a U-shape and placed above the gelatin gel with the end of the fiber bundle within the gelatin.

1 mL of 2% gelatin solution was added to the well, and the well plate was removed to a refrigerator until the gelatin solution gelled. Red food coloring was then added to each sample, and the fibers were examined for capillary action.

The red food coloring flowed through the bundles including wicking fibers, but did not flow through the bundles including fibers having a round cross section.

EXAMPLE 2

Fibers formed as described above in Example 1 were placed in a 12-well plate. D1 cells were trypsonized to an amount for $10^5$ per well and spun down to form cell pellets. A 3% alginate solution was formed. A collagen solution was prepared and used to dilute the alginate solution to 1.5%. 500 µL of an 0.05M $CaCl_2$ solution was poured into each well. The collagen solution was used to disperse the cell pellet. Collagen solution was mixed with alginate solution and the mixture was distributed to each well. The well plate was placed in a 37° C. incubator for one hour and 2 mL of culture was then added to each well. The cultures were allowed to develop in the wells, and medium was changed every two days.

After seven days, a live/dead assay was conducted according to a TEL protocol. Specifically, the gel/fiber system was removed to a 15 mL tube. 4 mL of 100 mM sodium citrate was added to the construct and incubated at 37° C. for 1 hour. The cells were spun down and dispersed by 1 mL of PBS. Cell number was obtained by use of a hemocytometer. Cell counts were obtained as shown below in Table 1.

| Sample | 1 | 2 | 3 | Average |
|---|---|---|---|---|
| Round fibers | 310000 | 235000 | 260000 | 270000 |
| Wicking fibers | 405000 | 510000 | 335000 | 420000 |

It will be readily understood by those persons skilled in the art that the present disclosure is susceptible of broad utility and application. Many embodiments and adaptations of the present disclosure other than those herein described, as well as many variations, modifications and equivalent arrangements, will be apparent from or reasonably suggested by the present disclosure and the foregoing description thereof, without departing from the substance or scope of the presently disclosed subject matter. Accordingly, while the present subject matter has been described herein in detail in relation to described embodiments, it is to be understood that this disclosure is only illustrative and exemplary of the present subject matter and is made merely for purposes of providing a full and enabling disclosure. The foregoing description is not intended or to be construed to limit the presently disclosed subject matter or otherwise to exclude any such other embodiments, adaptations, variations, modifications and equivalent arrangements.

What is claimed is:

1. A three-dimensional ex vivo or in vitro system comprising:
    a base material:
    a bundle of fibers comprising a plurality of wicking fibers embedded within the base material, each wicking fiber defining a plurality of colinear channels on the exterior surface of the wicking fiber, the colinear channels extending along the length of the exterior surface of the fiber, the bundle of fibers comprising the plurality of wicking fibers aligned with one another; and
    a plurality of ex vivo or in vitro cells, wherein
    the system supports the growth and development of the ex vivo or in vitro cells.

2. The three-dimensional ex vivo or in vitro system according to claim 1, wherein each wicking fiber is a hollow fiber.

3. The three-dimensional ex vivo or in vitro system according to claim 1, wherein the base material is a hydrogel.

4. The three-dimensional ex vivo or in vitro system according to claim 1, wherein the base material is an alginate sponge.

5. The three-dimensional ex vivo or in vitro system according to claim 1, wherein the system is sterile.

6. The three-dimensional ex vivo or in vitro system according to claim 1, further comprising one or more noncellular biologically active materials.

7. The three-dimensional ex viva or in vitro system according to claim 1, wherein the system is a fiber bioreactor system.

8. The three-dimensional ex viva or in vitro system according to claim 1, wherein the system is a component of a dialysis system.

9. The three-dimensional ex vivo or in vitro system according to claim 1, wherein the plurality of cells comprise a variety of cell types.

10. The three-dimensional ex vivo or in vitro system according to claim 1, wherein the plurality of cells are a portion of a tissue explant.

11. The three-dimensional ex vivo or in vitro system according to claim 1, wherein the base material is a gel matrix or a viscous fluid matrix.

12. The three-dimensional ex vivo or in vitro system according to claim 1, wherein the plurality of cells are autologous, allogenic, or xenogenic cells.

13. The three-dimensional ex vivo or in vitro system according to claim 6, wherein a noncellular biologically active material is covalently linked or associated by affinity to at least one of the base material and the bundle of fibers.

14. The three-dimensional ex vivo or in vitro system according to claim 1, wherein the cells are seeded on or in the wicking fibers.

15. The three dimensional ex vivo or in vitro system according to claim 1, wherein the cells are incorporated into the base material.

16. The three-dimensional ex vivo or in vitro system according to claim 1, further comprising a well comprising a liquid at one end of the bundle of fibers.

* * * * *